United States Patent
Klimes et al.

(10) Patent No.: US 6,171,238 B1
(45) Date of Patent: Jan. 9, 2001

(54) PORTABLE HAND-HELD DEVICE WITH A BIOSENSOR

(75) Inventors: Norbert Klimes; Dorothea Pfeiffer; Jan Szeponik; Jürgen Nentwig, all of Berlin; Frieder Scheller, Zepernick, all of (DE)

(73) Assignee: BST Bio Sensor Technologies GmbH, Berlin (DE)

( * ) Notice: Under 35 U.S.C. 154(b), the term of this patent shall be extended for 0 days.

(21) Appl. No.: 08/983,092

(22) PCT Filed: Jan. 26, 1996

(86) PCT No.: PCT/EP96/00328

§ 371 Date: Mar. 9, 1998

§ 102(e) Date: Mar. 9, 1998

(87) PCT Pub. No.: WO97/03355

PCT Pub. Date: Jan. 30, 1997

(30) Foreign Application Priority Data

Jul. 10, 1995 (DE) .......................................... 295 11 566 U

(51) Int. Cl.[7] .............................. A61B 5/05; G01N 27/26
(52) U.S. Cl. ....................... 600/345; 600/366; 73/863.01; 73/864.81; 73/864.83; 204/400; 204/403
(58) Field of Search .................................. 600/345, 352, 600/368, 300, 308, 309, 366, 365; 204/403, 415, 400, 409; 73/863, 864.81, 864.83

(56) References Cited

U.S. PATENT DOCUMENTS

| 3,787,291 | * | 1/1974 | Deuringer et al. | 204/409 |
| 4,533,456 | * | 8/1985 | Kratochvil et al. | 204/409 |
| 4,786,394 | * | 11/1988 | Enzer et al. | 204/403 |
| 5,074,157 | * | 12/1991 | Marsoner et al. | 204/409 |
| 5,089,421 | * | 2/1992 | Dieffenbach | 600/345 |
| 5,405,510 | * | 4/1995 | Betts et al. | 600/345 |

FOREIGN PATENT DOCUMENTS

| 4115792 | * | 11/1992 | (DE) . |
| 0520443 | * | 12/1992 | (EP) . |
| 2535964 | * | 5/1984 | (FR) . |

* cited by examiner

Primary Examiner—Cary O'Connor
Assistant Examiner—Navin Natnithithadha
(74) Attorney, Agent, or Firm—Horst M. Krasper

(57) ABSTRACT

The invention pertains to a portable hand device with biosensor for the investigation of biological fluids such as whole blood, liquor, urine and serum. It is characterized by a securely fixed electrode, which is covered by a replaceable biomembrane, as reservoir bag containing system solution and a waste bag, a pump, a tube transport system, an operating lever with a valve function, three operating elements, a display, and a control unit signal capture and overall procedure.

22 Claims, 3 Drawing Sheets

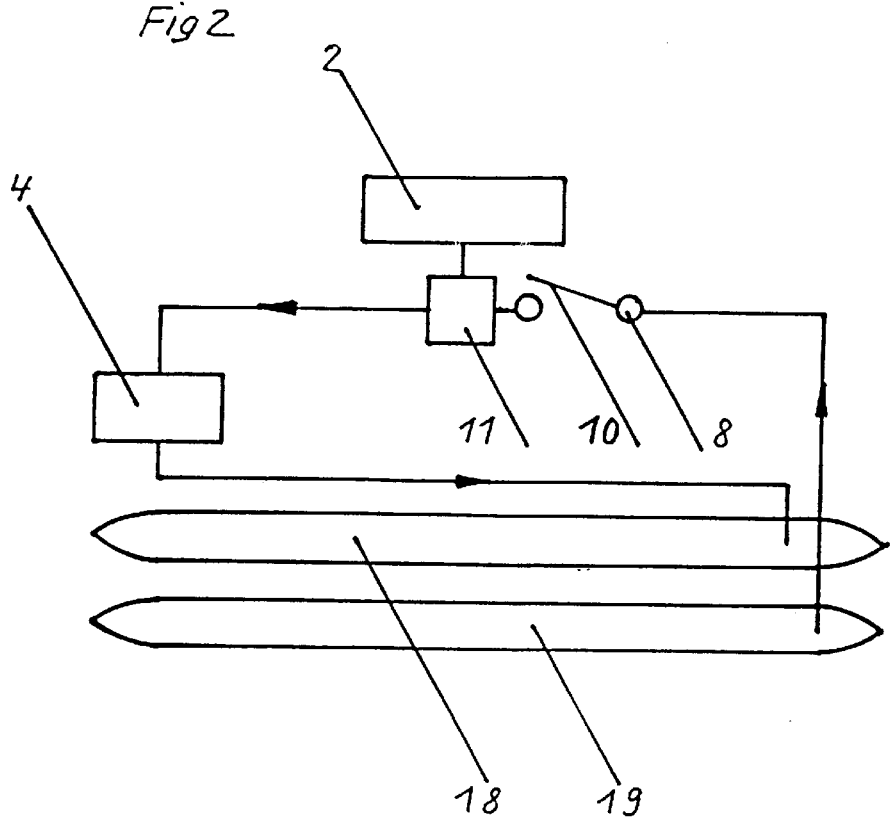
Fig 2
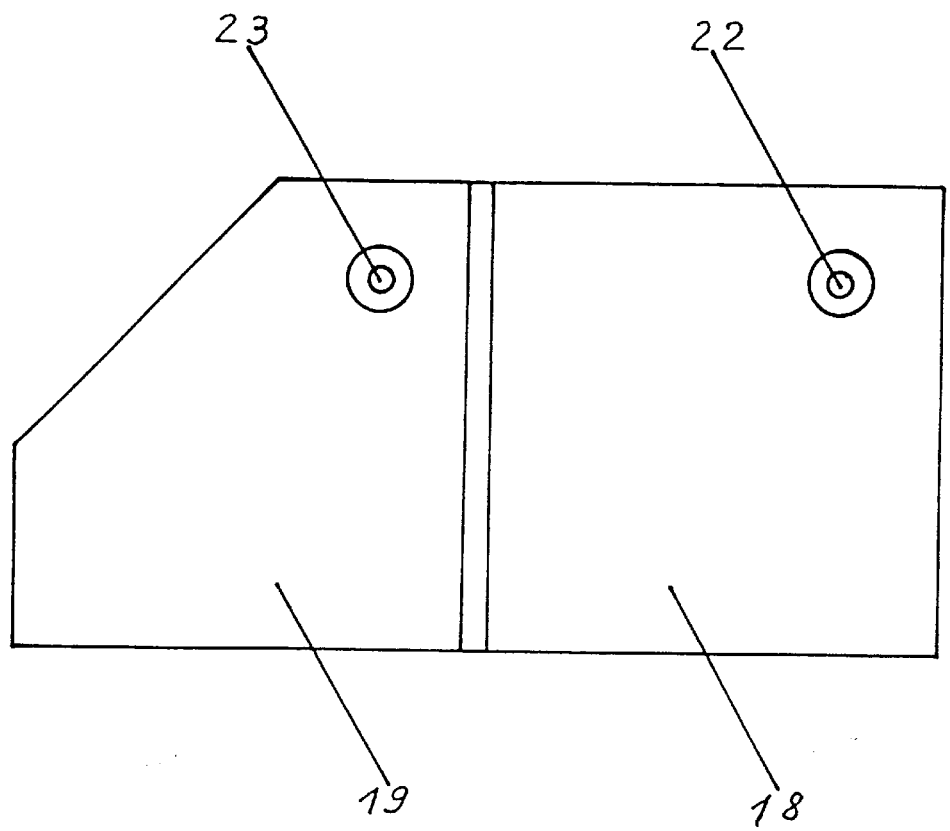

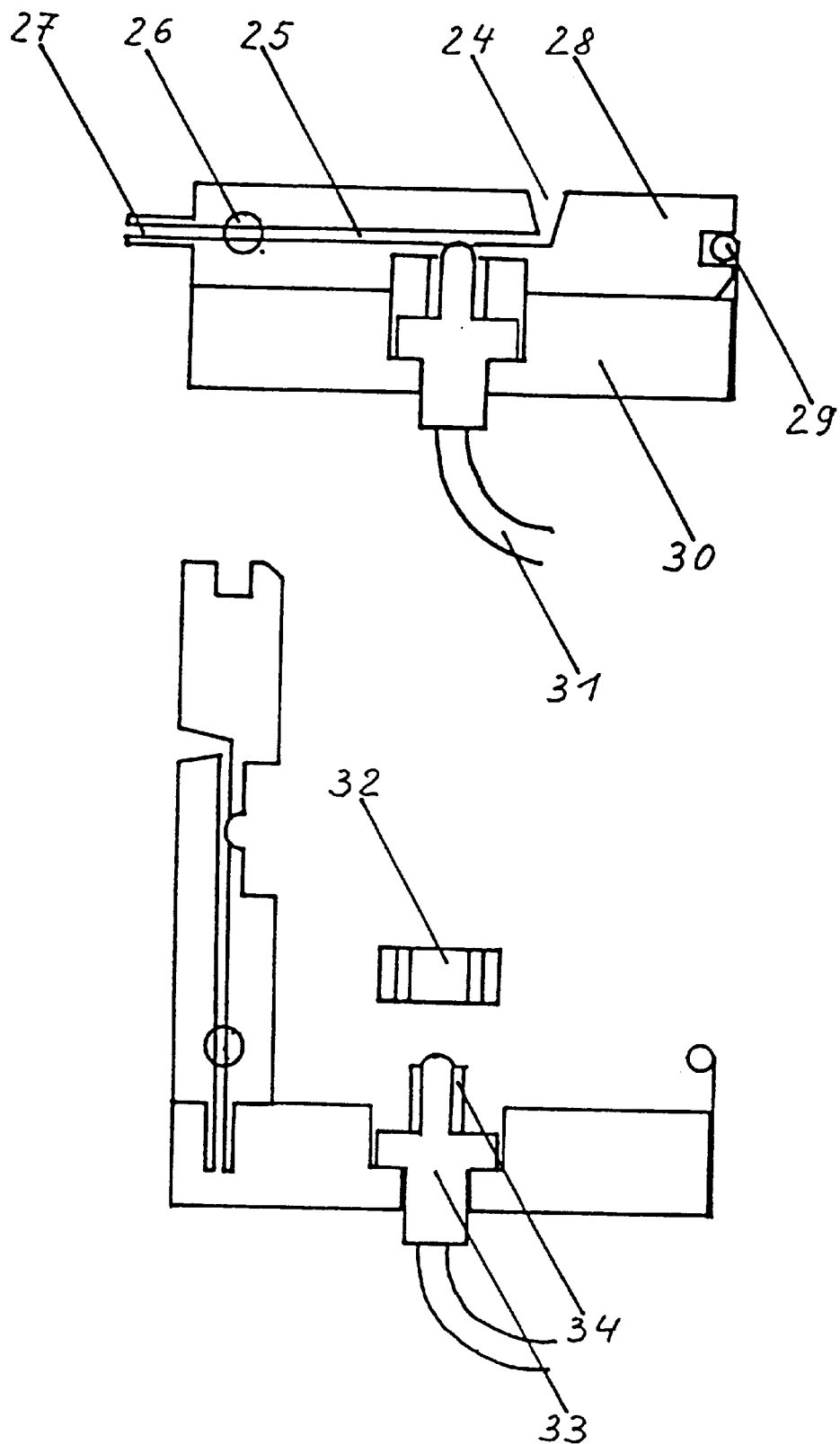

PORTABLE HAND-HELD DEVICE WITH A BIOSENSOR

BACKGROUND OF THE INVENTION

1. Field of the Invention

The invention concerns a hand-held equipment for the examination of biological liquids such as whole blood, liquor, urine and serum with the aid of electrochemical biosensors without costly preceding analysis being carried out.

2. Description of the Related Art

For a fairly long time biosensors have been applied as sensitive and selective detection methods in analysis, in particular of medical diagnostics. For this purpose, respective biosensors are installed in analyzers which allow to carry out a fast inexpensive and notably proper examination of the respective parameters in central laboratories where many samples have to be examined. This requires, as a rule, a sample throughput of 80 180/h.

The analyzers are based on various principles. For the most part, they are operated with a continuous air segmented flow of the respective, highly diluted laboratory samples, i.e. this method requires the preparation of the solutions to be examined (e.g. whole blood) with a dilution of the analysis material being required. It is very costly to analyze individual samples by means of this equipment as the efficiency of analyzers becomes effective only in the case of a high number of samples being examined (ESAT® 6660 and ECA 180 from Prüfgeräte-Werk Medingen GmbH, EBIO (Eppendorf® from Eppendorf-Netheler-Hinz GmbH).

Furthermore, there are instructions known to measure individual samples also without preceding analysis being carried out which, however, are very immovable owing to a high integrated measuring comfort, thus being unsuited for a local application (YSI 2300 STAT of YSI Incorporated and STAT Profile PLUS of NOVA BIOPMEDICAL GmbH).

From EP-A-0 520 443 a portable sensor equipment is known which consists of a waste collector, liquid canals and intakes and an electrochemical sensor in a case and an external calibration unit.

For the time being, commercialized mobile systems with integrated biosensors are too expensive owing to the high measuring comfort (internal calibration), require too much maintenance and are operated with too long transport ways for the sample to be measured. For this reason, in addition to a comparatively high price, delays and pollution will result which have detrimental effects on the quality of analyzing.

All measuring systems applied locally to determine parameters such as glucose and lactate are at present based on nonreusable consumables (test strips, photometric; strip electrode, amperometric). Thus the analysis is determined by the price of the test strip and the test strip is not calibratable as it may be used just once.

BRIEF SUMMARY OF THE INVENTION

That is why it was the task of the invention to provide a technical solution for implementing a locally applicable equipment for the examination of blood, urine, liquor without preceding analysis being carried out and a re-usable biosensor which is marked by a low price and also lowest maintenance costs.

The task will be solved by the construction of a hand-held equipment.

The hand-held equipment consists of a rigidly anchored electrode which is covered by a replaceable biodiaphragm, equipped with a system solution supply bag and a waste bag, a pump, a hose transport system, an operating lever with valve function, three operating elements, a display and a control unit for signal recording and the whole process. The equipment works with a temperature compensation. Thus, modified sensitivities of the biosensor are compensated through variations of the ambient temperature in the range between 15° C. and 35° C. on the basis of a signal-temperature function. Welded PE foils are preferentially used for the system solution and the waste, with the storage volume totalling approx. ⅓ and the waste volume approx. ⅔ of the total volume. In a preferential variant of execution the two bags are welded with each other. They are arranged one above the other and disposed jointly upon consumption of the buffer stock. The bag is opened when being installed the hand-held equipment through a hollow needle. When putting in a new supply bag the second half of the PE bag will be empty. In the same way as the stock will be consumed for purifying the measuring cell the waste bag will be filled. After having consumed the system solution completely the whole bag will be disposed.

The rigidly anchored electrode is a Pt-Ag/AgCl electrode of a CLARK electrode type. By combining it with a ready-made biodiaphragm by placing simply this the electrode is converted into a biosensor which may register various substances in accordance with the biomolecule used.

To execute a measurement the operating lever will be changed front idle position B (9) to position A (10), thus opening the flow system. By turning the pump into position I the electrode will be put into the state ready for measurement with the system solution in front of it having been sucked off.

The sample to be analyzed will be supplied with adjusting the freshly taken sample in a capillary tube to the sample opening of the hand-held equipment which is directly above the biosensor. Subsequently the pump is set in position II and the sample to be measured is transported by it in front of the biosensor. After effecting the measurement the result will be shown on the display and the operator will be requested to purify the system. The capillary tube is taken off by the user. By putting back the operating lever to position B the purification system is again closed. Purification itself is effected by turning the pump slowly until "ready for use" will appear on the display which is regarded to be a confirmation that the purification is completed and the pump will be in position III.

A hose pump is preferentially used as pump.

The three operating elements will be responsible for the following functions:

B1: on/off

B2: menu functions

B3: set key

Power supply will be possible through an internal 9V accumulator as well as an external solar cell or a supply unit. Depending on the biomolecule used a biodiaphragm has a limited lifetime which totals, in general, 10 to 30 days. The user will be shown the expiry of lifetime on the display. Upon expiry of its service life the biodiaphragm will be replaced by a new one.

The biodiaphragm is replaced by unlocking the respective sealing cap, taking off the worn-out diaphragm and simply placing a new diaphragm. By the information on the display the user will be informed on the steps necessary to take until the new diaphragm will be operative.

Signal recording and the whole process are controlled through a control unit. The whole process involves the beginning of signal recording (start), the end of signal recording, filing and storing of measured values, the calibration of the equipment and display information for the operator as regards the steps.

The hand-held equipment in conformity with the invention allows to carry out a minimum of 300 measurements without replacing the supply bag. A special advantage is that the equipment is usable in a temperature range between 15° C. and 35° C., independent of its place and time of use. In addition, the weight of the equipment is less than 500 g.

BRIEF DESCRIPTION OF THE DRAWINGS

The invention is explained in greater detail by means of the following examples of execution and drawings.

FIG. 2—Basic diagram of the equipment and arrangement of the supply and waste bags FIG. 3—View of electrode arrangement and representation of the replacement of the biodiaphragm

DETAILED DESCRIPTION OF THE INVENTION

Figure 1:
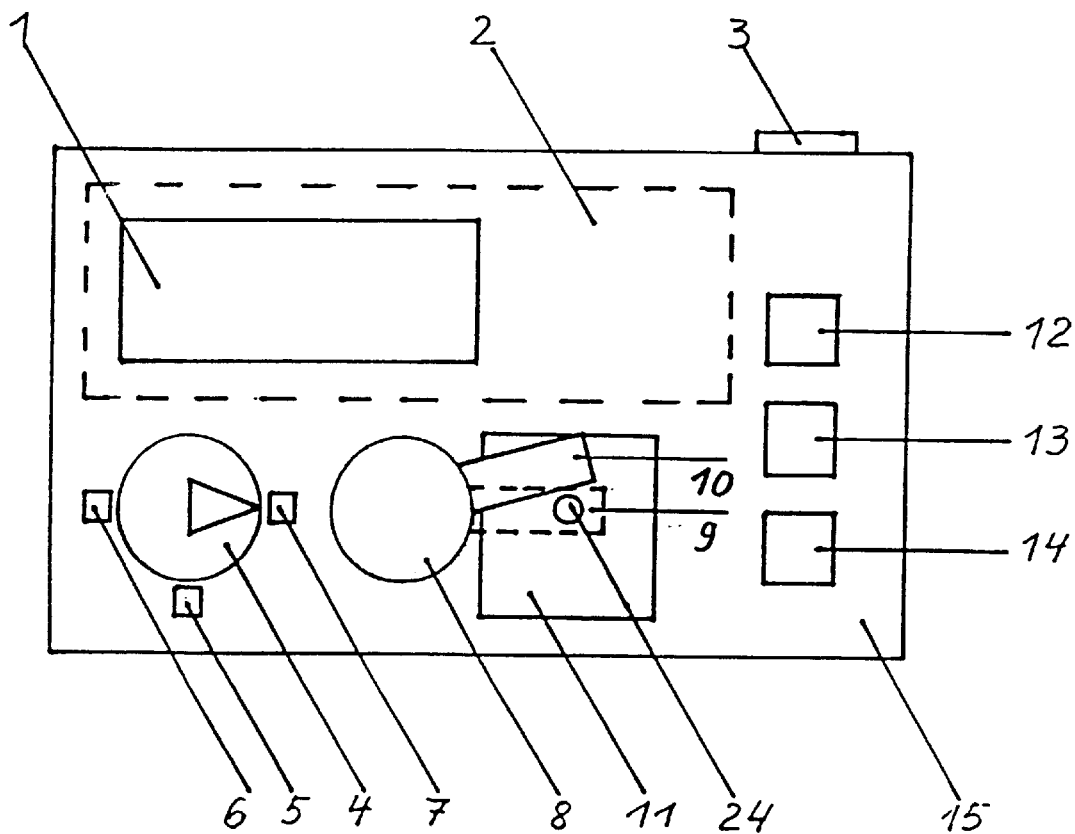
FIG. 1—Overall view of the hand-held equipment
Figure 1:
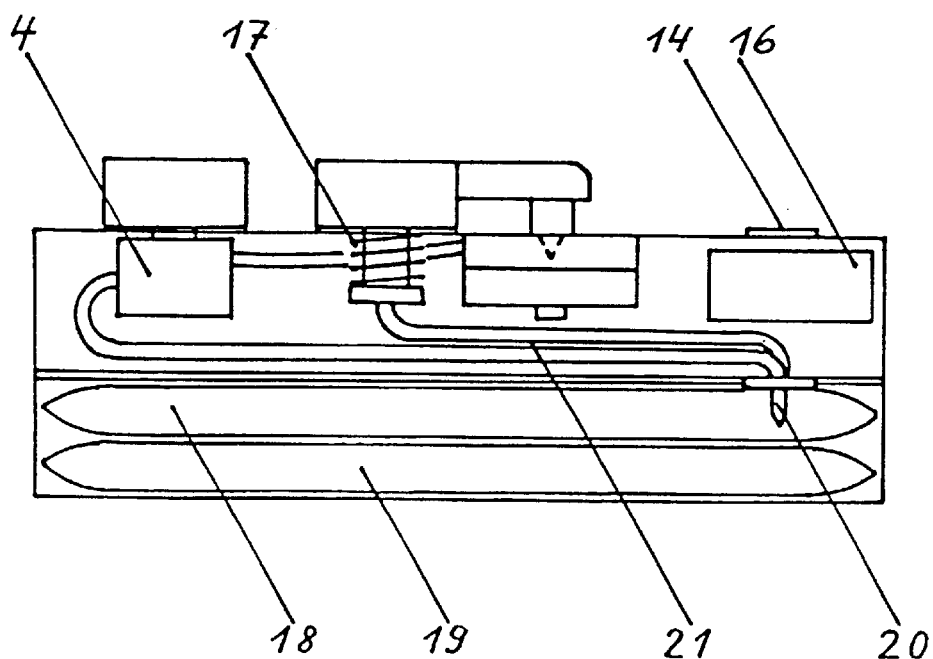

The hand-held equipment in conformity with FIG. 1 serves the examination of whole blood, liquor, tissue fluid, urine, serum, plasma, food samples as well as water samples as regards metabolites such as e.g. glucose, lactate; yet also nutrients and products of food and fermentation industries such as e.g. lactose, ascorbic acid, malic acid and various amino acids.

In FIGS. 1,2 and 3 the principle process of such a measurement is demonstrated. With the operating lever 8 opened (A-10) the buffer segment is put in position I (5) by pump 4, a hollow needle with the sample to be analyzed is put into opening 24, pump 4 is put in position II (6), and thus positioned in sample canal 25 above the biosensor 33 to start measurement. After completing measurement the measured value will be shown on the display (1) and the operator is requested to purify the system. For this purpose, the hollow sample needle is taken from opening 24, the operating lever 8 is put in position B (9) and by turning pump 4, the system solution is moved from the supply bag 19 through the hose transport system 21 into the waste bag. This contact of the biosensor with the buffer solution results in the purification of the sensor. The operator is informed on the termination of the purification by "ready for use" on display 1. Now, the pump is again put into idle position III (7). Thus, the hand-held equipment will be again ready for measuring and the following measurement will be effected according to the same scheme.

According to FIG. 3 the biodiaphragm may be again replaced upon expiry of the lifetime of a biomembrane (which is shown the operator on display 1). To this end, the operating lever 8 will be drawn upwards through spring 1 and turned upwards by 90°. Thus, it is possible to swing open by 90° the measuring cell cover 28 on axis 26 by releasing the fixing device 29. It is now possible to take off the worn-out biodiaphragm 32 and to put a new one on electrode 33 which is equipped with a rubber joint 34. Thereupon the measuring cell cover will be again swung down, stopped in 29 and the operating lever will be again put in position B (9). Thus the flow system will be again closed and by turning the pump system solution will be put on the biosensor for conditioning.

Reference marks:
1. display
2. plotting unit
3. connection for solar cell or supply unit
4. pump
5. pump position I
6. pump position II
7. pump position III
8. operating lever
9. operating lever—position B
10. operating lever—position A
11. measuring cell with biosensor
12. operating element B1
13. operating element B2
14. operating element B3
15. case
16. accumulator
17. spring for operating lever
18. waste bag
19. supply bag
20. hollow needle (connection between hose system, waste or supply bags)
21. hose system
22. seal for waste bag
23. seal for supply bag
24. sample opening
25. sample canal
26. axis
27. connection with the hose transport system (connection between sample canal and hose)
28. measuring cell cover
29. fixing device of the measuring cell cover
30. measuring cell bottom
31. connections for electrodes
32. biodiaphragm
33. electrode
34. electrode seal

What is claimed is:

1. Mobile hand-held equipment with biosensor, in particular for the local determination of original biological solutions, wherein a case (15), an amperometric biosensor (33) disposed in the case (15), a measuring cell (11) disposed in the case (15), a supply bag (19) and a waste bag (18) for fresh and waste system solution disposed in the case (15), a pump (4) placed in the case (15), a hose transport system (21) placed in the case (15), a sample opening (24) and a sample canal (25) placed in the case (15), an operating lever with valve function (8) attached to the case (15), equipment for replacing diaphragms (26, 27, 28, 29) placed in the case (15), a display (1) mounted to the case (15), on/off key button (12) placed on the case (15), menu function key button (13) placed on the case (15), set key button (14) placed on the case (15), a connector (3) for making a connection to a power supply (16), a unit for signal recording and the whole measuring process (2), and wherein welded PE foil is used for the supply bag (19) and the respective waste bag (18), the two bags are welded with each other, arranged one above the other and will be jointly disposed after the buffer stock will have been consumed.

2. Mobile hand-held equipment with biosensor according to claim 1, wherein the biosensor (33) is arranged directly below the sample opening (24).

3. Mobile hand-held equipment with biosensor according to claims 2 or 1, wherein the pump used (4) is operated by hand and without using electric energy.

4. Mobile hand-held equipment with biosensor according to claims 2 or 3, wherein the power supply of the electrode may be effected through a chargeable accumulator (16) as well as a solar cell, respectively, for forming a supply unit (3).

5. Mobile hand-held equipment with biosensor according to claims 2 or 1, wherein the weight of the equipment is less than 500 g.

6. Mobile hand-held equipment with biosensor according to claim 1, wherein the biosensor includes an electrode covered by a biodiaphragm.

7. A mobile hand-held equipment with a biosensor comprising
   a case;
   a connection for supplying power attached to the case;
   an on/off button attached to the case and connected to the connection for supplying power;
   a menu function key button attached to the case and connected to the on/off key button;
   a control unit disposed in the case;
   a set key button attached to the case and connected to the control unit;
   a measuring cell disposed in the case;
   a pump disposed in the case and connected to the measuring cell and to the menu function key button;
   a sample opening furnished at the case;
   a sample canal furnished at the case and led to the sample opening;
   a supply bag for delivering fresh system solution, wherein PE (polyethylene) is used for the supply bag and wherein the supply bag will be disposed after the system solution has been consumed;
   a valve disposed in the case;
   an operating lever attached to the valve and for actuating the valve;
   an amperometric biosensor disposed in the measuring cell;
   a waste bag for receiving discharged waste system solution, wherein PE (polyethylene) is used for the waste bag and wherein the waste bag will be disposed together with the supply bag after the system solution has been consumed;
   a hose transport system connected to the pump and to the supply bag;
   equipment for replacing diaphragms disposed in the case;
   a display disposed in the case and connected to the control unit;
   a unit for signal recording and the whole measuring process connected to the control unit.

8. The mobile hand-held equipment with biosensor according to claim 7,
   wherein the biosensor is arranged directly below the sample opening;
   wherein the pump used is operated by hand and without using electric energy;
   wherein welded PE foil is used for the supply bag and the waste bag, welded to each other, wherein the supply bag and the waste bag are arranged one above the other and wherein the supply bag and the waste bag will be jointly disposed after the buffer stock will have been consumed;
   wherein the power supply of the electrode is furnished by a chargeable accumulator and by a solar cell forming a supply unit;
   wherein the weight of the equipment is less than 500 g;
   wherein the sample opening is adapted to receive a capillary tube.

9. The mobile hand-held equipment with biosensor according to claim 7,
   wherein welded PE foil is used for the supply bag and the waste bag, welded to each other, wherein the supply bag and the waste bag are arranged one above the other and wherein the supply bag and the waste bag will be jointly disposed of after the system solution will have been consumed.

10. A mobile hand-held equipment with biosensor comprising
    a case;
    an electrode rigidly anchored in the case;
    a replaceable biodiaphragm covering the electrode and including a system solution supply bag and a waste bag;
    a pump attached to the case;
    a hose transport system attached to the case;
    an operating lever including a valve function supported at the case;
    three operating elements attached to the case;
    a control unit attached to the case for signal recording;
    a temperature compensation system for modifying sensitivities of the biosensor by furnishing compensation through variations of the ambient temperature the range between 15 degrees centigrade and 35 degrees centigrade on the basis of a signal temperature function.

11. The mobile hand-held equipment with biosensor according to claim 10 wherein a hose pump performs the functions of the pump.

12. The mobile hand-held equipment with biosensor according to claim 10 further comprising
    an electrical power supply;
    an on/off switch attached to the case for activating an electrical power supply;
    a menu function switch attached to the case for selecting operating modes of the mobile hand-held equipment with biosensor;
    a set key attached to the case for setting values for the operation of the mobile hand-held equipment with biosensor.

13. The mobile hand-held equipment with biosensor according to claim 12, wherein the power supply is an internal 9 volt accumulator.

14. A mobile hand-held equipment with biosensor comprising
    a case;
    an electrode rigidly anchored in the case;
    a replaceable biodiaphragm covering the electrode and including a system solution supply bag and a waste bag;
    a pump attached to the case;
    a hose transport system attached to the case;
    an operating lever including a valve function supported at the case;

three operating elements attached to the case;

a control unit attached to the case for signal recording;

wherein the system solution bag is made of polyethylene and wherein the waste bag is made of polyethylene;

wherein the storage volume is approximately one third of the total volume and wherein the waste volume is approximately one third of the total volume;

wherein the electrode is a Pt-Ag/AgCl electrode of a Clark electrode type.

15. A method for operating a hand-held-equipment with biosensor comprising installing a system solution supply bag in a hand-held equipment;

opening the system solution supply bag with a needle;

installing a waste bag in the hand-held equipment;

opening the waste bag with a needle;

consuming the system solution supply for purifying a measurement cell;

installing a replacement system solution supply bag when the currently installed system supply bag is substantially empty;

filling the waste bag in the same way as the system solution supply is being consumed from the system solution supply bag;

covering the electrode with a biodiaphragm and thereby converting the electrode into a biosensor, which registers various substances in accordance with the biomolecule used by combining a Pt-Ag/AgCl electrode of a Clark electrode type covered with a ready made biodiaphragm.

16. The method for operating a hand-held-equipment with biosensor according to claim 15, further comprising changing an operating lever from an idle position (B) to an operating position (A);

opening thereby the flow system;

turning a pump into a first position;

putting thereby the electrode into a state ready for measurement;

sucking off system solution in front of the electrode;

adjusting a freshly taken sample in a capillary tube to a sample opening of the hand-held equipment, wherein the sample opening is disposed immediately above the biosensor;

turning the pump into a second position;

transporting the sample to be measured with the pump in front of a biosensor;

performing a measurement;

displaying a result on a display;

requesting the operator to purify the system;

manually taking off the capitary by the user;

returning the operating lever into the idle position (B) and thereby closing the purification system.

17. The method for operating a hand-held-equipment with biosensor according to claim 16, further comprising turning the pump slowly into a third position until "ready for use" appears on the display and thereby effecting purification;

displaying an expiry of lifetime of a power supply on the display;

unlocking a respective sealing cap for replacing the biodiaphragm;

removing a worn-out biodiaphragm;

placing a new biodiaphragm.

18. The method for operating a hand-held-equipment with biosensor according to claim 15, further comprising opening an operating lever;

putting a buffer segment into a first position by a pump;

placing a hollow needle with a sample to be analyzed into an opening;

putting the pump into a second position;

thereby positioning the sample in a sample canal above the biosensor;

starting a measurement;

completing the measurement;

showing a measurement value on a display;

requesting the operator to purify the system;

taking the hollow needle from the opening;

putting the operating lever into an idle position;

turning the pump;

moving thereby system solution from a supply bag through a hose transport system into a waste bag;

purifying the biosensor by contacting the biosensor with a buffer solution;

informing the operator about the termination of purification by a signal "ready to use" on a display;

placing the pump into a third idle position.

19. The method for operating a hand-held-equipment with biosensor according to claim 15, further comprising replacing a biodiaphragm upon expiration of the lifetime of a biomembrane;

drawing the operating lever upwards through a spring;

turning the operating lever upward by 90 degrees;

swinging a cover of the measuring cell open by 90 degrees around an axis;

releasing a fixing device;

taking off a worn-out biodiaphragm;

putting a new biodiaphragm on the electrode equipped with a rubber joint;

swinging the cover of the measuring cell down again;

stopping the cover of the measuring cell;

placing the operating lever again in an idle position;

thereby closing again the flow system;

turning the pump;

thereby putting system solution on the biosensor for conditioning.

20. A mobile hand-held equipment with biosensor comprising a case;

an electrode rigidly anchored in the case;

a replaceable biodiaphragm covering the electrode and including a system solution supply bag and a waste bag;

a pump attached to the case;

a hose transport system attached to the case;

an operating lever including a valve function supported at the case;

three operating elements attached to the case;

a control unit attached to the case for signal recording;

wherein welded PE foil is used for the supply (19) and the respective waste bags (18), the two bags are welded with each other, arranged one above the other and will be jointly disposed after the buffer stock will have been consumed.

21. Mobile hand-held equipment with biosensor, in particular for the local determination of original biological solutions, wherein a case (15), an amperometric biosensor (33) disposed in the case (15), a measuring cell (11) disposed in the case (15), supply (19) and waste bags (18) for fresh and waste system solution disposed in the case (15), a pump (4) placed in the case (15), a hose transport system (21) placed in the case (15), a sample opening (24) and a sample canal (25) placed in the case (15), an operating lever with valve function (8) attached to the case (15), an equipment for replacing diaphragms (26, 27, 28, 29) placed in the case (15), a display (1) mounted to the case (15), on/off key button (12) placed on the case (15), menu function key button (13) placed on the case (15), set key button (14) placed on the case (15), a connector (3) for making a connection to a power supply (16), consisting of an accumulator and a solar cell or another supply unit, a plotting unit for signal recording and the whole measuring process (2), and wherein welded PE foil is used for the supply (19) and the respective waste bags (18), the two bags are welded with each other, arranged one above the other and will be jointly disposed after the buffer stock will have been consumed.

22. A method for operating a hand-held-equipment with biosensor comprising installing a supply/waste system, consisting of a supply bag welded with a waste bag;

opening both bags with a needle;

consuming the system solution supply for purifying a measurement cell;

exchanging the supply waste system, when the currently installed system is nearly empty, which is indicated by a display reading;

covering the electrode with a biodiaphragm and thereby converting the electrode into a biosensor, which registers various substances in accordance with the biomolecule used by combining a Pt-Ag/AgCl electrode of a Clark electrode type covered with a ready made biodiaphragm.

* * * * *